United States Patent [19]

D'Hondt

[11] Patent Number: 4,630,229
[45] Date of Patent: Dec. 16, 1986

[54] CIRCUIT FOR THE FAST CALCULATION OF THE DISCRETE FOURIER TRANSFORM OF A SIGNAL

[75] Inventor: Jean-Pierre D'Hondt, Tournai, Belgium

[73] Assignee: Intercontrole Societe Anonyme, Rungis, France

[21] Appl. No.: 467,761

[22] Filed: Feb. 18, 1983

[30] Foreign Application Priority Data

Feb. 23, 1982 [BE] Belgium .............................. 0/207387

[51] Int. Cl.[4] .......................... G06F 7/34; G06F 15/35
[52] U.S. Cl. ................................................. 364/726
[58] Field of Search ................ 364/576, 725, 726, 827

[56] References Cited

U.S. PATENT DOCUMENTS

| | | | |
|---|---|---|---|
| 3,636,333 | 1/1972 | Klund | 364/726 |
| 3,754,128 | 8/1973 | Corinthios | 364/726 |
| 4,084,251 | 4/1978 | Gillis, Jr. | 364/726 |
| 4,117,541 | 9/1978 | Ali | 364/726 |
| 4,138,730 | 2/1979 | Ali | 364/726 |
| 4,199,660 | 4/1980 | Dill et al. | 370/50 |
| 4,266,279 | 5/1981 | Hines | 364/726 |
| 4,298,985 | 11/1981 | Ballard et al. | 364/485 |
| 4,328,555 | 5/1982 | Nussbaumer | 364/726 |
| 4,334,273 | 6/1982 | Ikeda | 364/726 |
| 4,479,229 | 10/1984 | Wolter | 364/827 |

OTHER PUBLICATIONS

Stearns, *Digital Signal Analysis*, pp. 50–71, Hayden Book Company Inc., Rochelle Park, N.J., 1975.
Stearns, *Digital Signal Analysis*, pp. 265–268, Hayden Book Company Inc., Rochelle Park, N.J., 1975.

*Primary Examiner*—James D. Thomas
*Assistant Examiner*—Dale M. Shaw

[57] ABSTRACT

A circuit for the rapid calculation of the real and imaginary parts of the h first harmonics of a signal supplied by a measuring device and particularly for the analysis of the voltage supplied by a non-destructive eddy current testing probe. The circuit comprises an analog-digital converter, a random access memory, and calculating means comprising a PROM, a counter, a multiplier, an accumulator and a sequencer.

4 Claims, 6 Drawing Figures

CIRCUIT FOR THE FAST CALCULATION OF THE DISCRETE FOURIER TRANSFORM OF A SIGNAL

BACKGROUND OF THE INVENTION

The present invention relates to a circuit for the fast calculation of the discrete Fourier transform of a signal. It is used more particularly in the analysis of measuring signals, particularly in the analysis of the voltage supplied by a non-destructive eddy current testing probe.

It is known that this type of testing involves producing a variable magnetic field with the aid of a primary winding, subjecting a member to be tested to the field and sampling a voltage at the terminals of a secondary winding positioned in the vicinity of the tested member and analyzing this voltage. The primary and secondary windings are located in a probe, whose structure can be in different forms (they may coincide, be arranged in bridge-like manner, etc). Any defect in the tested member (change of size, variation of the electrical conductivity, variation of the magnetic permeability, cracks, etc) modifies the phase and intensity of the eddy currents induced in the member and correlatively changes the voltage sampled at the terminals of the probe.

When the member to be tested is magnetic, a special difficulty linked with the high permeability of material is encountered. This leads to the measuring signal being made dependent on certain parameters, such as the size, weight, etc.

In the case of the testing of magnetic members, the processing of the measuring signal essentially consists of the determination of its harmonics. In other words, it consists of a Fourier transformation. It has been shown that the knowledge of the harmonics of the signal makes it possible to obviate the aforementioned disadvantage with regard to the dependence of the measurement on certain parameters. Thus, the amplitude of the third harmonic, which reflects relatively well the structure of the part, but which remains sensitive to the weight thereof, can be weighted by the phase or amplitude of the fundamental term, which is a function of the weight of the part, in order to obtain a result which is substantially independent of the weight. Other combinations between harmonics make it possible to obtain freedom from other parameters. It is also known that the first harmonic component plays a predominant part. In an impedance plane, it can be represented by a point which, in the case of the passage of the member through a differential transducer, describes a figure eight curve, whose amplitude and orientation make it possible to determine defects of the tested member.

In a more general way, the circuit according to the invention is used at the output of a measuring device, like that illustrated in FIG. 1. A random measuring device 110 supplies an analog measuring signal at an output 111. A signal processing circuit 120 has an input 121 connected to output 111 and to output 122, which supplies information relative to the harmonics of the measuring signal. The preferred field of the invention is the non-destructive testing by eddy currents. In this case, device 110 comprises an alternating current generator 112, followed by an amplifier circuit 113 supplying a probe 114. The members to be tested 116 pass in the vicinity of probe 114. The measuring signal sampled by the probe is amplified by a circuit 118 and appears at output 111. It is this signal which is applied to the analysis circuit 120. A circuit 124 for processing the results can complete the analysis circuit in order to act on a sorting member 125 able, for example, to eject defective members.

The analysis circuit 120 performs a Fourier transformation of the signal applied to it. Although analog analysis circuits are possible, preference is now given to digital circuits, which make it possible to obtain a better accuracy and a greater flexibility of analysis. The signals to be processed are firstly converted into digital samples and then undergo the transformation in question. As this operation not takes place on a sequence of samples and not on a continuous quantity, it is conventionally called discrete Fourier transformation (DFT).

In block 120, FIG. 1 illustrates the block diagram of an analysis circuit of this type, which comprises an analog-digital converter 126, a random access memory 128, which will subsequently be referred to as an acquisition memory, which has a data input 129 connected to converter 126 and an output 131, a means 140 able to perform a discrete Fourier transformation on the samples contained in memory 128, said transformation making it possible to determine the real part R and the imaginary part I of the harmonics of the signal.

In order to provide a better understanding of the originality of the invention, it is necessary to give brief details on the discrete Fourier transformation.

It is a question of calculating a harmonic component $X_k$, in which k is the rank of the harmonic in question from a sequence of samples x(n), in which n designates the rank of the sample in the sequence, whereby said rank ranges from 0 for the first sample to N-1 for the last. The harmonics of rank k is given by the standard expression:

$$X_k = \frac{1}{N} \sum_{n=0}^{N-1} x(n) \cdot \exp\left(-j\frac{2\pi nk}{N}\right)$$

in which N designates the number of samples used for the calculation, the letter j being the symbol of the imaginary parts. By developing the exponential function, it becomes:

$$X_k = \frac{1}{N} \sum_{n=0}^{N-1} x(n) \left[\cos\frac{2\pi nk}{N} + j\sin\frac{2\pi nk}{N}\right]$$

which makes it possible to separate the real part $R_k$ and imaginary part $I_k$ of the harmonic of rank k:

$$R_k = \frac{1}{N} \sum_{n=0}^{N-1} x(n) \cos\frac{2\pi nk}{N}$$

$$I_k = \frac{1}{N} \sum_{n=0}^{N-1} x(n) \sin\frac{2\pi nk}{N}$$

The amplitude A and the phase $\phi$ of the harmonic in question can be gathered from the knowledge of $R_k$ and $I_k$:

$$A = \sqrt{R^2 + I^2}$$

$$\phi = \text{arctg}\frac{I}{R}$$

The calculation of both R and I necessitate in each case N multiplicatons, because the N samples must be taken singly. It is therefore necessary to carry out 2N multiplications per harmonic. As it is possibile to calculate N harmonics with a sequence of N samples, a total discrete Fourier transformation consequently requires 2N² multiplications.

It is obvious that this number becomes very large when N is high. For example, for 512 samples, it is equal to 524,288. Thus, the calculation time becomes prohibitive and the testing device cannot operate in real time.

It is for this reason that no fast eddy current testing device based on discrete Fourier transformation uses the calculating rules referred to hereinbefore, which constitute theoretical definitions of the quantities to be calculated rather than operating principles for the circuits used. High performance equipment uses more complicated algorithms intended to reduce the calculating time. The transformation performed is then called "fast" or fast Fourier transform (FFT).

The algorithms used are known and there is no need to refer to them here (COOLEY, SANDE and similar algorithms). It is merely pointed out that they involve factorizations of matrices using intermediate coefficients between the signal and its transform. Thus, calculation takes place in stages, the first starting with N samples and the last leading to N harmonic components. Thus, the number of operations performed in these algorithms is reduced and ranges from $2N^2$ to $2N \log_2 N$. For N=512, this number is equal to 13,824, as compared with 524,288 on the basis of the previously defined rules.

BRIEF SUMMARY OF THE INVENTION

The object of the present invention is to further speed up the calculation of the harmonics. To this end and completely paradoxically, the invention does not use the fast Fourier transformation referred to hereinbefore and instead uses the aforementioned elementary process considered to be inappropriate. Thus, the invention runs counter to the prejudices of the art, which always recommended fast algorithms passing through intermediate stages.

The invention results from a detailed analysis performed by the inventors, of the specific nature of the discrete Fourier transformation in the case of non-destructive testing by eddy currents. The special feature of this method is that it only requires the first harmonics of the signal and not all the N harmonics giving the usual fast Fourier transformation. Thus, the question which arises is to know how many operations the fast Fourier transformation requires on limiting the development to the first harmonics.

A detailed study of the generally used algorithms and which would fall outside the scope of the present application, shows that in the case where the number of samples N is equal to a power of $2(N=2^b)$, in order to obtain the h first harmonics with an FFT algorithm, it is necessary to carry out a number of operations equal to:

$$\sum_{i=0}^{b} |h \cdot 2^i| \text{ limited to } N$$

in which i represents the number of stages used in the fast algorithm, the quantity $h \cdot 2^i$ being limited to value N.

For h=3, i.e. when interest is only attached to three harmonics, the fast Fourier transformation requires 3795 operations. However, the sample operations of direct products of the samples by coefficients in sine and cosine require $3 \times 2 \times 512 = 3072$ operations, which is a lower figure. This gives the surprising result that the simple multiplication algorithm is faster than the fast transformation algorithms in this special situation.

The first inventive idea on which the present invention is based is consequently to work in reality on the following expressions:

$$R_k = \frac{1}{N} \sum_{n=0}^{N-1} x(n) \cos \frac{2\pi nk}{N}$$

$$I_k = \frac{1}{N} \sum_{n=0}^{N-1} x(n) \sin \frac{2\pi nk}{N}$$

i.e. to form the products of samples x(n) by coefficients cos $2\pi nk/N$ and sin $2\pi nk/N$ and form the sums on the products obtained.

These operations could be performed with the aid of an instruction program relating to multiplications (to obtain the products in question) and additions (to form the sum of the products obtained). However, for reasons of rapidity, the invention recommends another solution, which is the use of a special wired circuit, essentially constituted by a multiplier, followed by an accumulator. The interest of such a solution is that it is possible to use circuits operating in wired logic manner, which are much faster than program-based circuits. The calculating time of these circuits can be approximately 100 nanoseconds.

A supplementary interest provided by the invention is that it makes it possible to use certain commercially available circuits which are able to perform both multiplications, additions and an accumulation in a very short time.

With regard to the sine and cosine coefficients necessary for the calculations, they can be produced by a program. The invention also prefers to use a circuit, in the present case a memory, in which are stored all the coefficients used. This memory is of the programmable read only memory type (PROM). It is subdivided into the same number of blocks as there are harmonic components to be calculated, the blocks of rank k containing the coefficients of index k necessary for the calculation of the $k^{th}$ harmonic.

Finally, the addressing of the two memories in which are stored the samples and coefficients could be carried out by instructions from a control microprocessor. This solution would involve a preparation time of roughly 100 $\mu$s and would cancel out the advantage of using a multiplier operating at 100 ns. According to the invention, the reading of the two memories takes place with the aid of the same counter, which very rapidly supplies the successive addresses of the samples and coefficients.

Thus, the structure of the entire calculator or computer according to the invention is based on the desire of obtaining a high calculating speed, despite the apparent slowness of the calculating process adopted.

Thus, specifically, the present invention relates to a circuit for the rapid calculation of the discrete Fourier transform of a signal supplied by a measuring device, particularly a non-destructive eddy current testing device, in which the circuit comprises:

an analog-digital converter having an input receiving the signal to be processed and an output supplying digital samples;

a random access memory, called an acquisition memory, having a data input connected to the output of the converter, an addressing input and a data output;

means for calculating the discrete Fourier transform having an input connected to the output of the acquisition memory and an output supplying the real part and the imaginary part of the harmonics of the signal, wherein the means for calculating the discrete Fourier transform comprises:

a programmable read-only memory, called the coefficient memory, having an addressing input and a data output, said memory being subdivided into the same number of blocks as there are harmonics to be calculated, the kth block containing the coefficients sin $2\pi nk/N$ and cos $2\pi nk/N$, in which N is the number of samples contained in the acquisition memory and in which N assumes all the values ranging from 0 to N-1, a counter having two outputs carrying two sets of addresses, the first output being connected to the addressing input of the acquisition memory and the second to the addressing input of the coefficient memory, said addresses respectively corresponding to the samples of the acquisition memory and to the coefficients of a coefficient memory block, a multiplier circuit having two inputs, one connected to the output of the acquisition memory, the other connected to the output of the coefficient memory, and an output, an accumulator circuit having an input connected to the output of the multiplier and an output carrying the sought real and imaginary parts, a sequencer circuit able to transmit the pulses to the counter, to control the reading of the samples in the acquisition memory and, simultaneously, the reading in the first block of the coefficient memory of the coefficients cos $2\pi n/N$, then to again control the reading of the samples in the acquisition memory and simultaneously the reading in the first block of the coefficient memory of coefficients sin $2\pi n/N$ and, for each reading of a sample and a coefficient, to control the multiplier and then the accumulator and then reiterate these operations with the second block of the coefficient memory and so on up to the last.

BRIEF DESCRIPTION OF THE DRAWINGS

The invention is described in greater detail hereinafter relative to non-limitative embodiments and the attached drawings which show in.

DETAILED DESCRIPTION OF THE PREFERRED EMBODIMENTS

The invention can be used whenever it is desired to rapidly calculate the first harmonic components of a measuring signal. This is the case in the non-destructive testing by eddy currents, which is a particularly preferred application and for this reason the present description will be based on this example.

Figure 1:
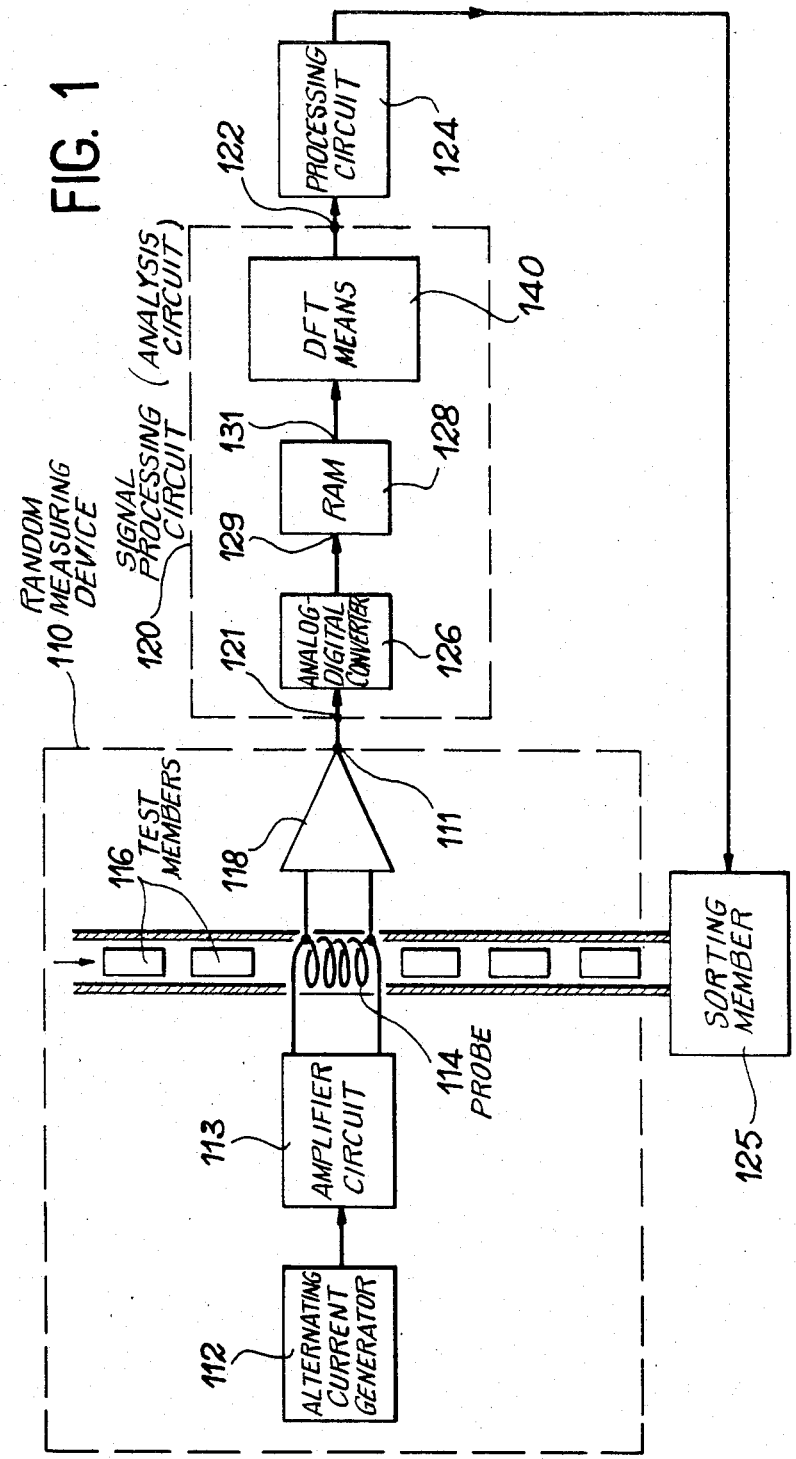
FIG. 1 a measuring device and analysis circuit (already described)
Figure 2:
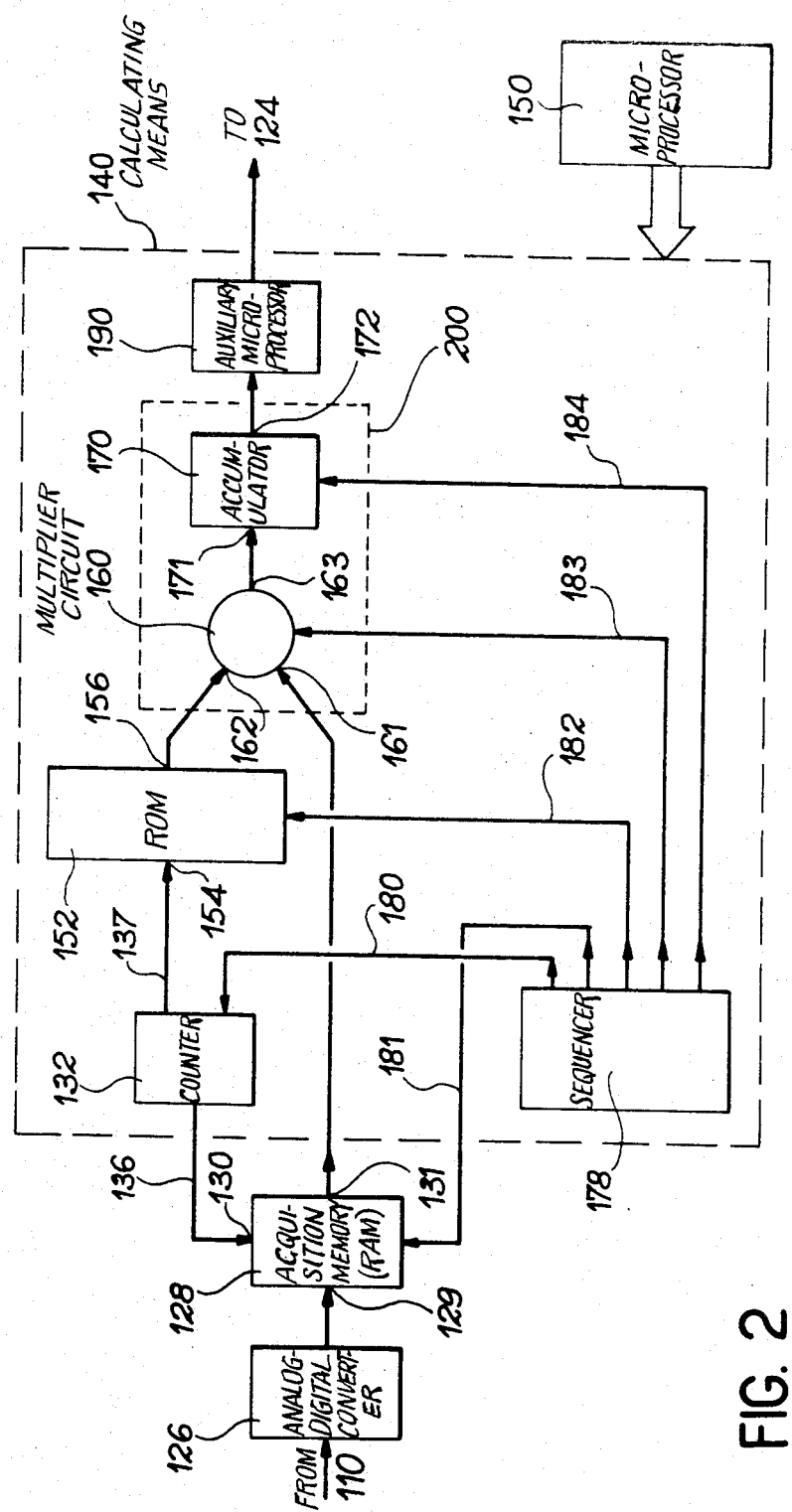
FIG. 2 the block diagram of the calculating or computing circuit according to the invention.

The general diagram of the circuit according to the invention is illustrated in FIG. 2 in which it is also possible to see the elements already described in connection with FIG. 1, namely the analog-digital converter 126 and the acquisition memory 128. FIG. 2 more specifically illustrates the structure of the means 140 making it possible to calculate the real and imaginary parts of the first harmonics from N samples stored in acquisition memory 128.

As shown, means 140 essentially comprises a read only memory 152, a counter 132, a multiplier 160, an accumulator 170 and a sequencer 178 and these elements will now be described in detail.

The read only memory 152 of the PROM type has an addressing input 154 and a data output 156. This memory is divided into the same number of blocks as there are harmonics to be calculated (in the present case three blocks). The kth block contains the coefficients sin $2\pi nk/N$ and cos $2\pi nk/N$, in which N is the number of samples contained in the acquisition memory 128 and in which n assumes all the values ranging from 0 to N-1. In the first block, there are the coefficients sin $2\pi n/N$ and cos $2\pi n/N$, in the second block the coefficients sin $4\pi n/N$ and cos $4\pi n/N$ and in the third block the coefficients sin $6\pi n/N$ and cos $6\pi n/N$.

Counter 132 has two outputs carrying in each case a set of addresses. The first output 136 is connected to an addressing input 130 of acquisition memory 128 and the second 137 to the addressing input 154 of coefficient memory 152. The addresses supplied by counter 132 respectively determine a sample in the acquisition memory 128 and a coefficient in one of the blocks of the coefficient memory 132. For N=512, it is necessary to have 9 bit addresses ($2^9$=512). In order to select one block from among 3, it is also necessary to have two addressing bits and for selecting either the sine sequence or the cosine sequence, it is necessary to have a further addressing bit, i.e. in all $9+2+1=12$ bits for addressing memory 152.

The multiplier circuit 160 has two inputs 161 and 162, the first connected to output 131 of acquisition memory 128 and the second to output 156 of coefficient memory 152. The multiplier also has an output 163.

The accumulator circuit 170 has an input 171, which is connected to output 163 of multiplier 160 and an output 172 which carries the real and imaginary parts of the sought harmonics.

The sequencer circuit 178 is connected by a connection 180 to the counter 132, by a connection 181 to the acquisition memory 128, by a connection 182 to the coefficient memory 152, by a connection 183 to multiplier 160 and by a connection 184 to accumulator 170.

The means also comprises a microprocessor 150, which is connected to all the aforementioned elements (by connections which are not shown in FIG. 3 for simplification reasons, but which will appear in the following drawings).

By means of connection 180, sequencer 178 addresses the counting pulses to the counter 132. By connection 181, it controls the reading in acquisition memory 128 and simultaneously the reading of coefficients in memory 152.

The reading of the samples and coefficients in their respective memories is obtained by counter 132, whose content evolves from 0 to 511 under the control of the pulses which it receives from the sequencer.

The sequencer firstly controls the reading of samples in cosine. For each pulse, a sample and a coefficient in cosine simultaneously appear at multiplier inputs 161, 162. By connection 183, the sequencer then instructs multiplier 160 to form the product of the two data. Then, by connection 184, the sequencer controls accumulator 170, which takes into account the partial product supplied by the multiplier.

On the following pulse addressed to the counter, a new sample appears at the multiplier input and also a new coefficient in cosine. The multiplication and accumulation operations are reproduced.

After 512 cycles of this type, the sequencer informs microprocessor 150 that a complete calculation has been performed and that the real part of the first harmonic is present at output 172 of accumulator 170. Microprocessor 150 then reads the result and instructs the sequencer to carry out the following sequence making it possible to obtain the imaginary part.

For this purpose, by means of an appropriate signal carried by connection 182, the sequencer selects the sequence of coefficients in cosine, still in the first block of the coefficient memory. After 512 new reading, multiplication and accumulation operations, the accumulator supplies the imaginary part of the first harmonic. The microprocessor 150 reads this result and instructs the sequencer to carry out the calculation phase of the second harmonic.

It is then the reading of the second block of the coefficient memory 152 which is addressed and the two calculation sequences are reproduced. Finally, the third block of memory 152 is addressed, which makes it possible to obtain the real and imaginary parts of the third harmonic.

In certain cases, it is desirable to calculate the amplitude and phase of each harmonic. Rather than use the microprocessor 150 with the aid of calculation routines, which would lead to the calculations lasting longer, the invention recommends the use of an auxiliary microprocessor 190 (FIG. 2) which, bearing in mind the particular task which it has to fulfil, may be wired accordingly and which is consequently very fast. It is a so-called mathematical microprocessor able to perform the operations of raising to the square (to obtain $R^2$ and $I^2$) addition (to obtain $R^2+I^2$), extraction of the square root (to obtain the modulus of the harmonic), calculating a quotient (of I by R) and calculating the arc tangent of the quotient obtained (to obtain the argument of the harmonic in question).

The knowledge of these three harmonics, on the basis of their amplitude and phase, makes it possible by suitable algorithms to obtain the aforementioned combinations representing the quality of the tested member. Naturally, the means downstream of the accumulator output 172 are dependent on the envisaged application and could differ from those described hereinbefore.

In practice, it is possible to combine multiplier 160 and accumulator 170 on the same integrated circuit, designated symbolically by block 200. Such circuits are commercially available. For example, it can consist of circuit TDC 1010J marketed by the U.S. Company TRW. One of the interests of the presses invention is that it permits the use of such high performance circuits, particularly with regard to the calculation speed.

The central microprocessor 150 is linked with the acquisition memory 128, the coefficient memory 152, the multiplier 160 and the accumulator 170, so that it is possible to use these components for tasks other than those required by the aforementioned harmonic analysis. These links are more readily apparent in FIG. 3 which shows groups of connections or buses, with the necessary interface circuits.

Figure 3:
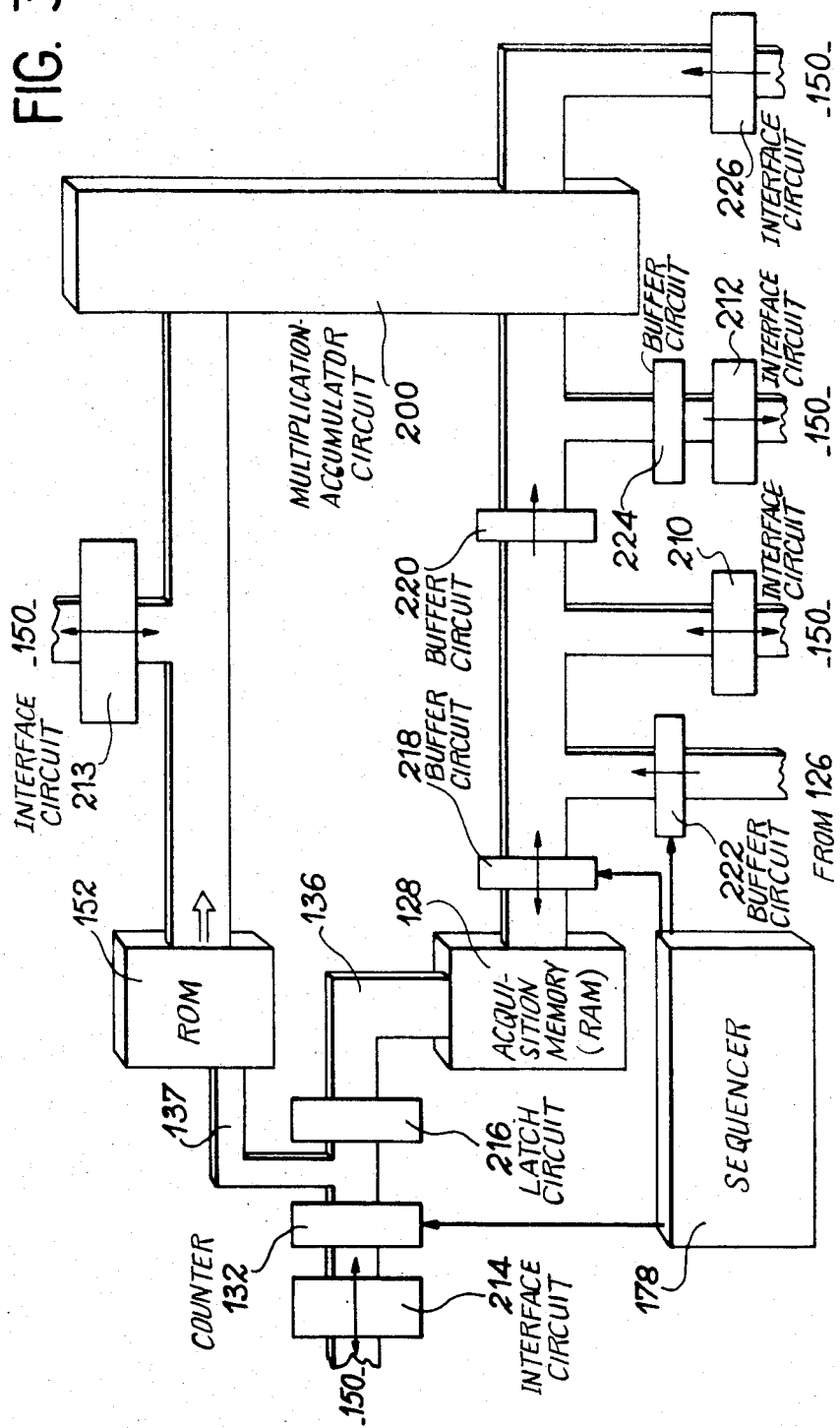
FIG. 3 a general diagram of a variant.

In FIG. 3 are shown an interface circuit 210 enabling the circuit to read and write in acquisition memory 128, and iterface circuit 212 enabling the microprocessor to read the calculating results in circuit 200, another interface circuit 213 giving access to the coefficient memory 152, an interface circuit 214 giving access to counter 132, a latch circuit 216 (which is transparent with respect to the signal applied thereto and which stores the latter), bidirectional buffer circuits 218, 220 positioned at the output of memory 128 and at the input of circuit 200, a unidirectional buffer circuit 222 positioned on the data bus from converter 126 and making it possible to write the data in memory 128, a unidirectional buffer circuit 224 located on the bus and giving the microprocessor access to the calculating circuit 200 and finally an interface circuit 226 permitting the introduction of data and control instructions into circuit 200 by means of the microprocessor.

The interest of enabling the microprocessor to read in the memories is that it becomes possible to chose therein one from among many coefficients or samples. In particular, it is possible to store a weighted set of coefficients or samples, the weighing being chosen so as to compensate for the effects of the limitation imposed on the measuring signal (limitation to N samples), whereby said artificial limitation can comply with certain known criteria (Hamming function, etc). The microprocessor then determines which is the most appropriate set for the problem to be solved. Moreover, the access to counter 132 makes it possible to load the latter to a chosen initial content.

Figure 4:
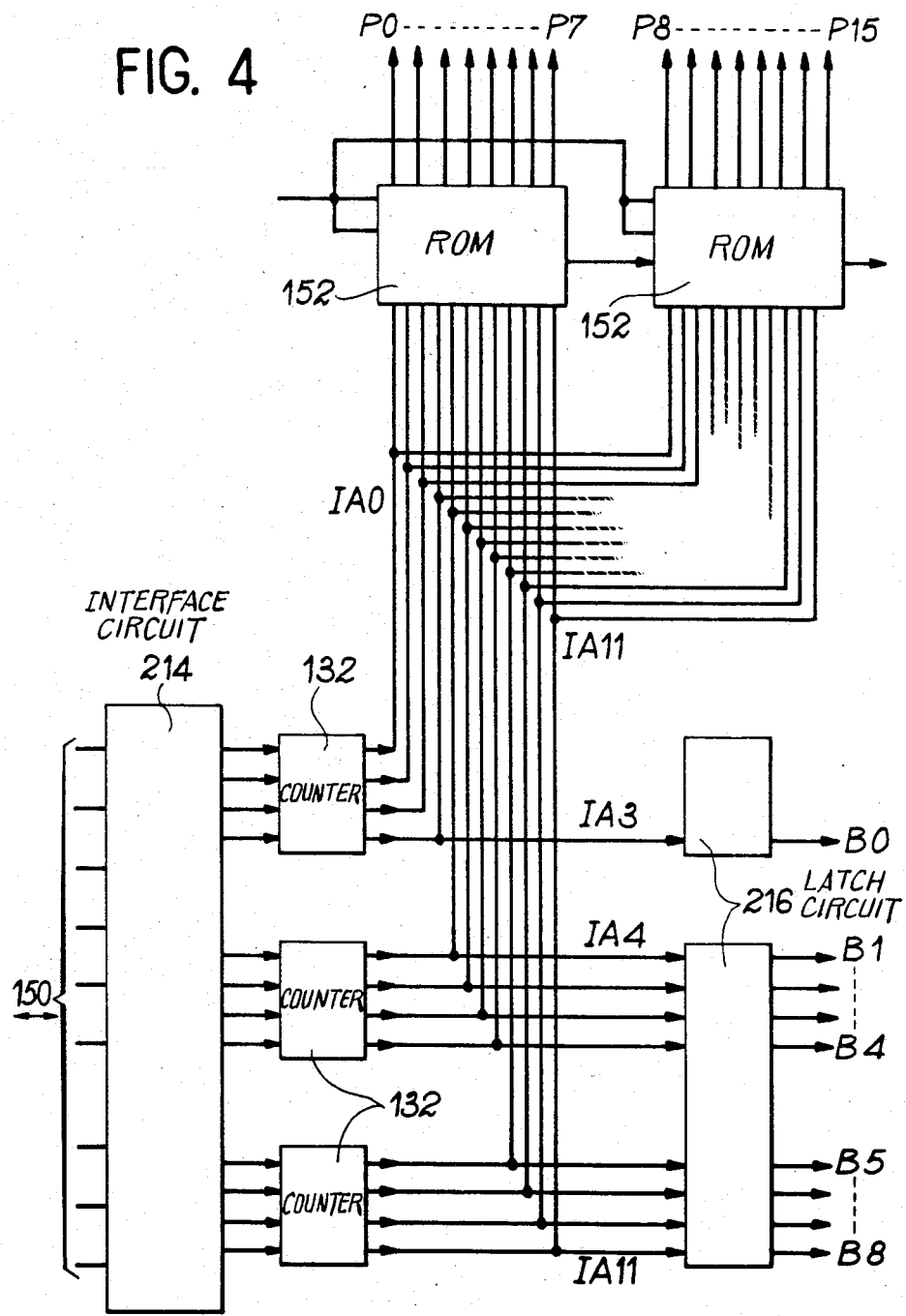
FIG. 4 a special embodiment of an addressing counter and a coefficient memory.
Figure 5:
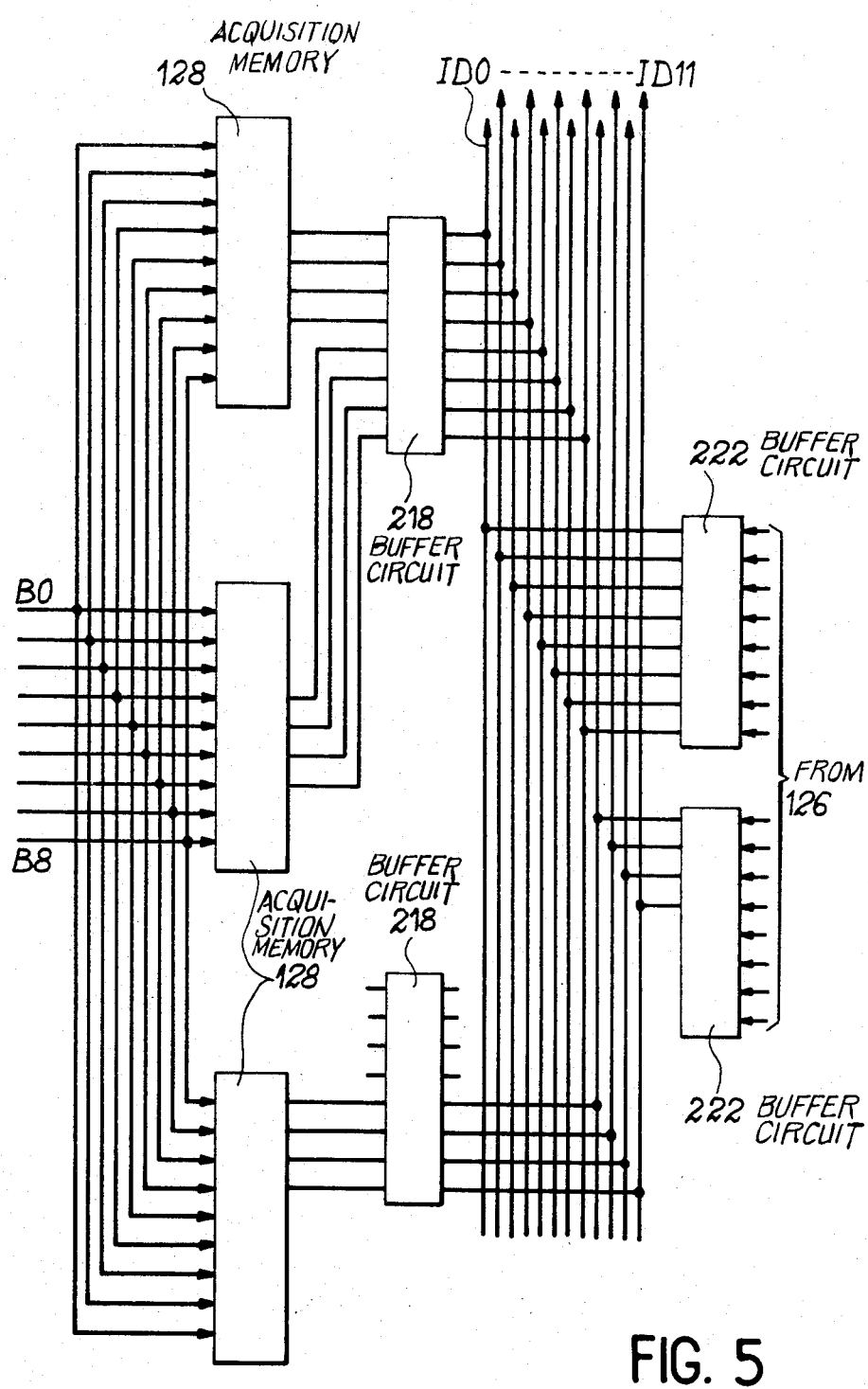
FIG. 5 an embodiment of an acquisition memory.
Figure 6:
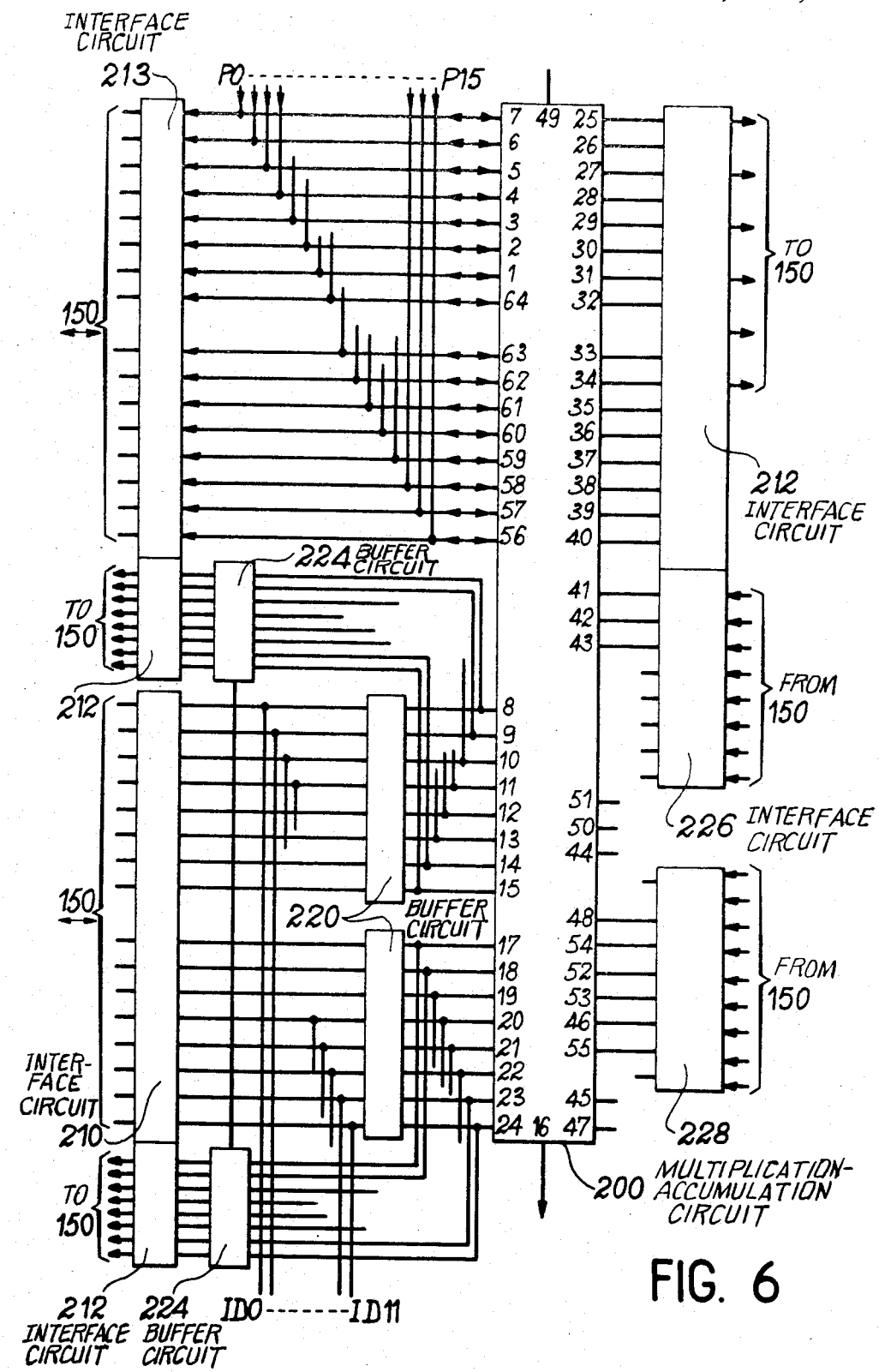
FIG. 6 an embodiment of the calculating circuit and its associated input-output circuits.

FIGS. 4 to 6 illustrate in a more specific manner the special embodiments of the circuit according to the invention in the following case. The calculations are performed with 512 samples. The multiplication-accumulation circuit 200 functions with 16 bits. The result is given with 35 bits. The acquisition memory operates with 12 bit words and the coefficient memory with 15 bit words (it would also be possible to use 16 bit words, because circuit 200 accepts them, but there would be a risk of an overflow in the accumulator).

FIG. 4 firstly shows interface circuit 214 (which is e.g. of type 8255) followed by counter 132 formed by three partial counters with 4 outputs (e.g. of type 74 LS 191), giving a total of $3\times4=12$ address connnections designated IA0, IA1 . . . IA11. On the one hand, these 12 connections are directed straight to the coefficient memory 152 and on the other hand, with respect to the 9 connections IA3 to IA11, to the acquisition memory via the latch circuit 216 (comprising e.g. a circuit 74 LS 373 for the final 8 connections IA4 to IA11 and a circuit 74 LS 75 for connection IA3). The 9 addressing outputs for the acquisition memory are designated B0, B1 . . . B8. The coefficient memory 152 can comprise two memory circuits (e.g. of type 2732), each addressed by 12 connections IA0 to IA11. The 12 addressing bits are subdivided into two bits defining one of the three coefficient blocks, one bit defining the sequence in cosine or in sine in the chosen block and 9 bits defining one coefficient from among the 512 in the chosen sequence. The memory supplies words of $2\times8=16$ bits, whereof only 15 are used. The output coefficients are designated P0 to P15.

FIG. 5 shows the area around the acquisition memory 128 in a construction using three storage circuits (e.g. of type 2114) with 4 outputs each. This memory is addressed by 9 inputs B0, B1 . . . B8. The 3×4=12 inputs-outputs are connected to a buffer circuit 218 formed by bidirectional circuits (type 8286 with 4 inputs-outputs and type 81 LS 95 which has 8 inputs 0 outputs). The discharge of the samples read takes place via the 12 outputs ID0, ID1 . . . ID11.

FIG. 6 shows the calculating circuit 200 and its inputs-outputs. This circuit, which is the master part of the means, comprises for example TDC 1010J supplied by TRW. This circuit has 64 accesses 1 to 64. Accesses to 1 to 7 and 56 to 64 operate either as inputs, in which case they receive the coefficients by connections P0 to P15, or as outputs, in which case they supply the most significant bits of the result to the interface circuit 213 connected to the microprocessor. Accesses 8 to 15 and 17 to 24 also operate on an input-output basis. As inputs, they receive the samples, by connections ID0 . . . ID11 across buffer circuit 220 (which can comprise two circuits of type 81 LS 95). As outputs, they supply the least significant bits of the result across buffer circuit 224 and then across interface circuit 212 to the microprocessor. The other accesses on the right hand side enable the microprocessor to have access to the components of circuit 200. All the interface circuits can be of type 8255.

The sequencer is not shown because it is of a known type. It comprises a high stability quartz oscillator, followed by dividers, making it possible to produce pulses at various frequencies. The oscillator can be a circuit 74 LS 124 and the dividers circuits 74 LS 123.

The analog-digital converter also operates with 512 samples per cycle on 12 bits. For an operating frequency between 3 and 3000 Hz, this conversion can cause problems at the top of the range, because it is then necessary to convert 300×512 samples per second. This problem can be solved by taking the samples over several cycles instead of one cycle, which is possible because the signal is cyclic. The number of cycles used for conversion purposes can be programmed and determined by the microprocessor.

The digital nature of the structure described hereinbefore, its speed and its informatized character lead to a testing device having a very considerable flexibility of use. It has a wide range of possibilities:

it is possible for each tested member to represent the real and imaginary parts of a harmonic by a point of coordinates R and I in an impedance plane and to accumulate the points for the different tested members, it then being possible to show quality tendencies relative to the tested members at the time of manufacture, a processing of the display can easily be obtained by displacement, elimination, setting of points, etc, when the harmonic or harmonics are processed via their amplitude and phase, it is possible to numerically record these two quantities or to show them graphically, when a special sorting algorithm has been used, the result can be displayed and located in a tolerance range, each displayed result can be allocated a number permitting an identification of the members, the microprocessor assists the operator in his work by indicating the limits which must not be exceeced, by safety checks, etc;

a printer can be connected to the device for producing a production journal, which can show various statistics, developments, tendencies, etc.

finally, the device can be connected to external memories, e.g. flexible disks for the recording of the results obtained, which makes it possible to produce an exhaustive file of the tests.

What is claimed is:

1. A circuit for the rapid calculation of the real and imaginary parts of the h first harmonics, h being 3 at most, of a signal supplied by a measuring device, particularly a non-destructive eddy-current testing device, said circuit comprising:

an analog-digital converter having an input receiving the signal to be processed and an output supplying digital samples, a random access, acquisition memory having a data input connected to the output of the converter, an addressing input and a data output, means for calculating the discrete Fourier transform having an input connected to the output of the acquisition memory and an output supplying the real part and the imaginary part of the harmonics of the signal, said means for calculating the discrete Fourier transform comprising:

a programmable read-only, coefficient memory having an addressing input and a data input, said coefficient memory being subdivided into h blocks, the kth block, with k integer between 1 and h, containing the coefficients $\sin 2\pi nk/N$ and $\cos 2\pi nk/N$, in which N is the number of samples contained in the acquisition memory and in which n assumes all the values ranging from 0 to N-1, a counter having two outputs carrying two sets of addresses, the first output being connected to the addressing input of the acquisition memory and the second to the addressing input of the coefficient memory, said addresses respectively corresponding to the samples of the acquisition memory and to the coefficients of a coefficient memory block, a multiplier circuit having two inputs, one connected to the output of the acquisition memory, the other connected to the output of the coefficient memory, and an output, an accumulator circuit having an input connected to the output of the multiplier circuit and an output carrying the sought real and imaginary parts, a sequencer circuit able to transmit pulses to the counter, to control the reading of the samples in the acquisition memory and, simultaneously, the reading in the first block of the coefficient memory of the coefficients $\cos 2\pi n/N$, and then to against control the reading of the samples in the acquisition memory and simultaneously the reading in the first block of the coefficient memory of coefficients $\sin 2\pi n/N$ and, for each reading of the sample and a coefficient, to control the multiplier and then the accumulator and then reiterate the controlling and reading with the second block of the coefficient memory and so on up to the last block.

2. A circuit according to claim 1, comprising, connected to the accumulator output, a mathematical calculation microprocessor able to perform the following operations:

raising to the square of the real and imaginary parts received from the accumulator, addition of the squares obtained, extraction of the square root from the sum obtained, calculation of the quotient of the imaginary part by the real part, and calculation of the arc tangent of the quotient obtained.

3. A circuit according to claim 1, comprising a microprocessor having accesses to the memories, to the counter, to the multiplier, to the accumulator and to the sequencer.

4. A circuit according to claim 1, wherein the multiplier and accumulator are constituted by the same integrated circuit.

* * * * *